(12) United States Patent
Glynn

(10) Patent No.: US 8,382,713 B2
(45) Date of Patent: Feb. 26, 2013

(54) DRUG DELIVERY DEVICE AND METHODOLOGY

(75) Inventor: Kenneth P. Glynn, Flemington, NJ (US)

(73) Assignee: Kenergy Scientific, Inc., Flemington, NJ (US)

( * ) Notice: Subject to any disclaimer, the term of this patent is extended or adjusted under 35 U.S.C. 154(b) by 1606 days.

(21) Appl. No.: 11/637,275

(22) Filed: Dec. 11, 2006

(65) Prior Publication Data

US 2008/0140007 A1 Jun. 12, 2008

(51) Int. Cl.
*A61M 5/20* (2006.01)
(52) U.S. Cl. .................................................. 604/135
(58) Field of Classification Search ............... 604/135, 604/236, 191, 249, 196, 33, 82, 167.01, 187, 604/89, 256, 195; 251/149.1, 318, 321, 344, 251/347, 324
See application file for complete search history.

(56) References Cited

U.S. PATENT DOCUMENTS

| | | | |
|---|---|---|---|
| 3,425,664 A * | 2/1969 | Niskin | 251/344 |
| 3,542,023 A | 11/1970 | Ogle | |
| 3,980,083 A | 9/1976 | Elliot | |
| 4,592,745 A | 6/1986 | Rex et al. | |
| 5,374,250 A * | 12/1994 | Dixon | 604/110 |
| 5,478,316 A | 12/1995 | Bitdinger et al. | |
| 5,637,094 A | 6/1997 | Stewart, Jr. et al. | |
| 6,030,363 A | 2/2000 | Kriesel | |
| 6,132,395 A * | 10/2000 | Landau et al. | 604/68 |
| 6,196,477 B1 * | 3/2001 | Halltorp et al. | 239/579 |
| 6,599,268 B1 | 7/2003 | Townsend et al. | |
| 6,632,198 B2 | 10/2003 | Caizza | |
| 6,669,671 B1 | 12/2003 | Mohammad | |
| 6,676,641 B2 | 1/2004 | Woodard, Jr. | |
| 6,685,677 B2 | 2/2004 | Green | |
| 6,752,782 B2 | 6/2004 | Liao | |
| 6,776,775 B1 | 8/2004 | Mohammad | |
| 6,805,689 B2 | 10/2004 | Chen | |
| 6,846,301 B2 | 1/2005 | Smith et al. | |
| 6,863,659 B2 | 3/2005 | Sharpe | |
| 6,872,190 B1 | 3/2005 | Denis et al. | |
| 6,926,696 B2 | 8/2005 | Mohammed | |
| 2004/0111054 A1 * | 6/2004 | Landau et al. | 604/68 |
| 2005/0020984 A1 * | 1/2005 | Lesch, Jr. | 604/187 |

* cited by examiner

*Primary Examiner* — Christopher D Koharski
(74) *Attorney, Agent, or Firm* — Kenneth P. Glynn, Esq.; Deirda M Meagher, Esq.

(57) ABSTRACT

Drug delivery devices adapted to receive liquid medication to fill a reservoir, utilize sliding through valves that are closed except when driven by force of liquid medication pushed by a plunger to an open position to feed the medication via needle to a patient or via a connection to an IV port. The devices have multiple seals and automatically close up when pressure on the plunger is released. The methodology is also included.

18 Claims, 8 Drawing Sheets

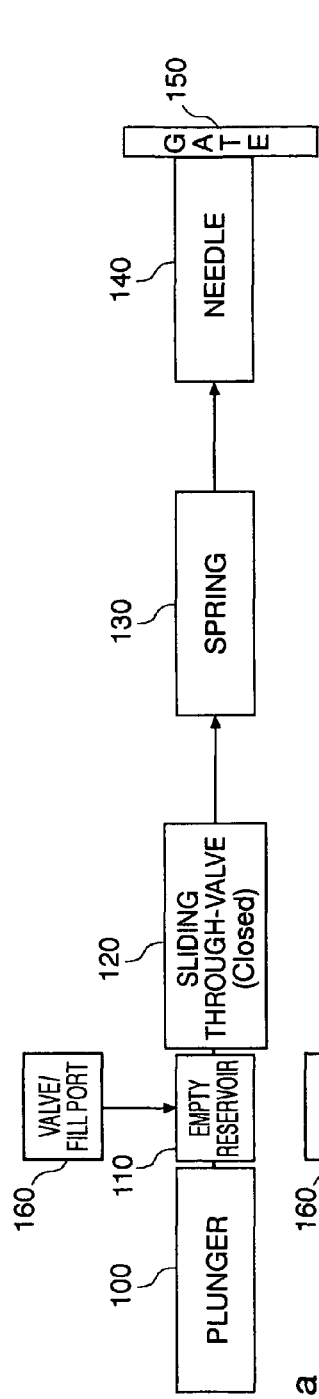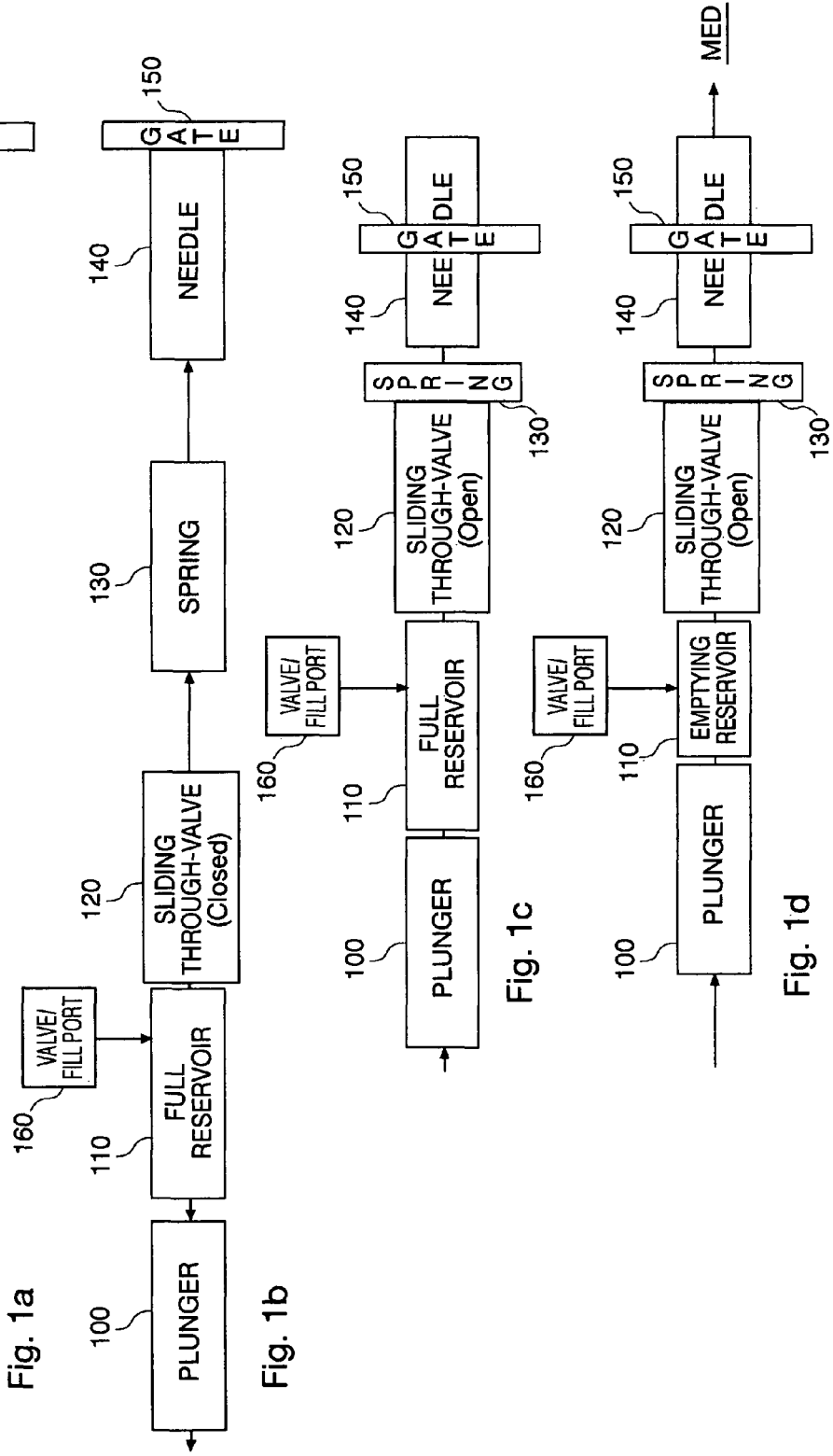

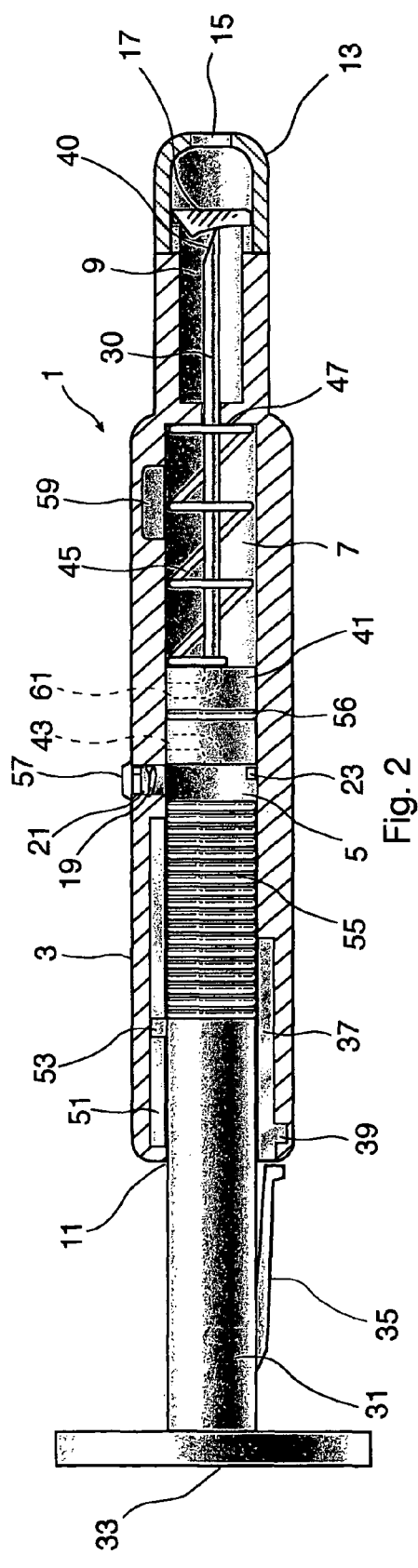
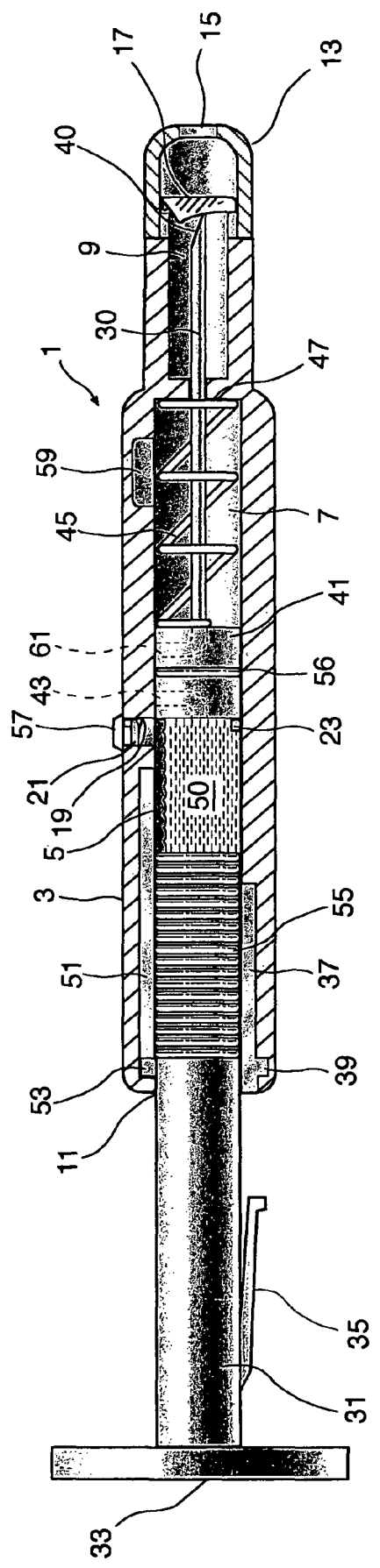
Fig. 2
Fig. 3

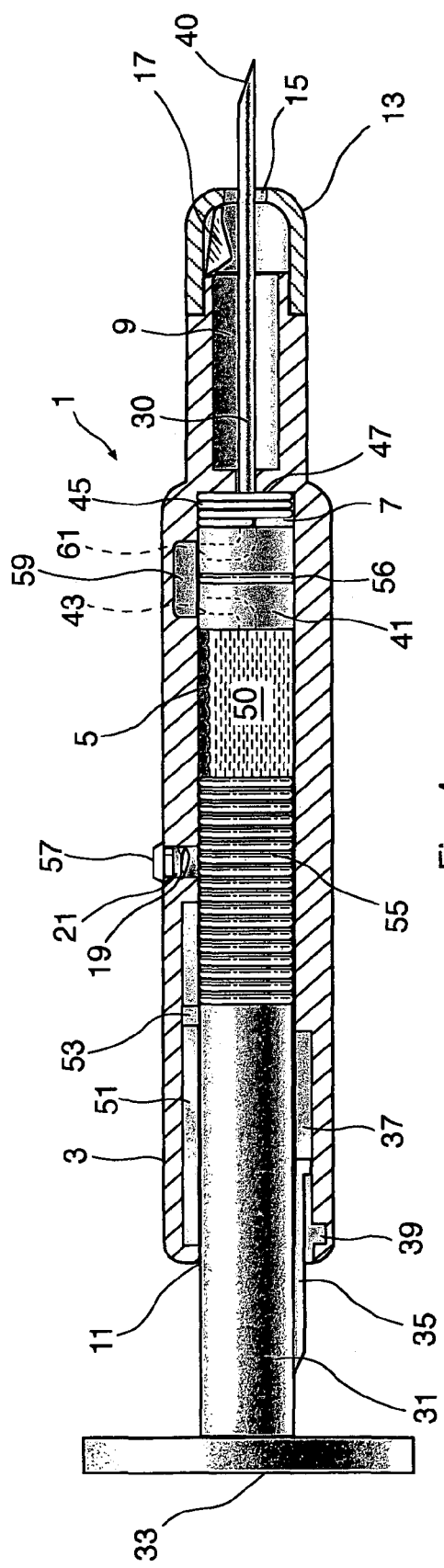
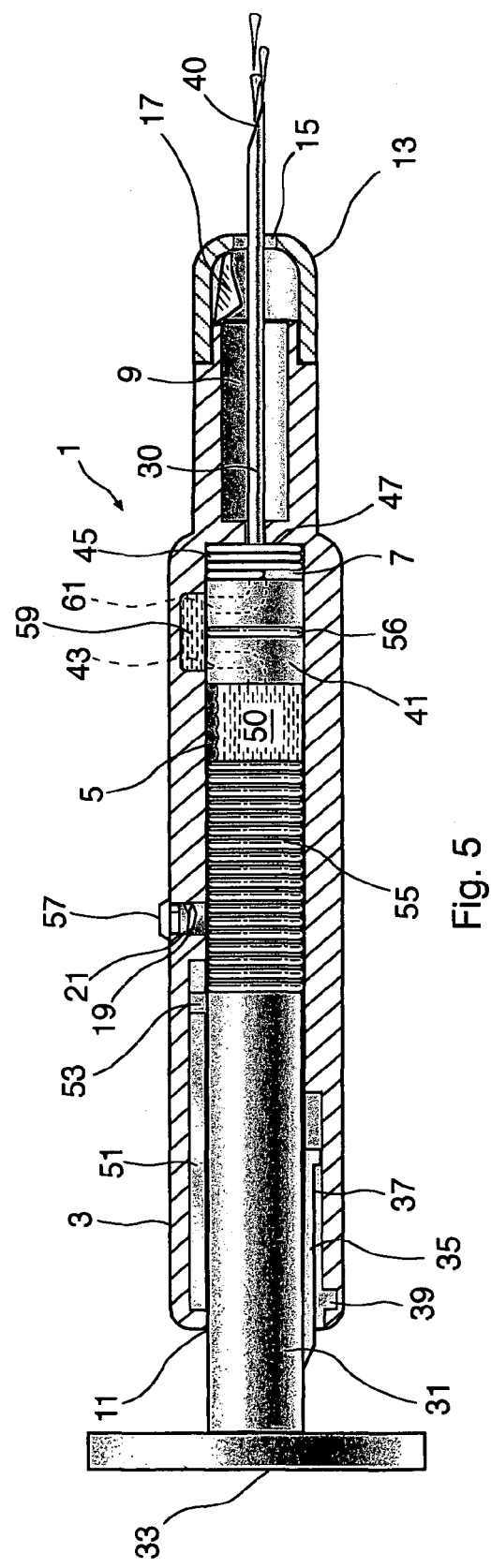
Fig. 4
Fig. 5

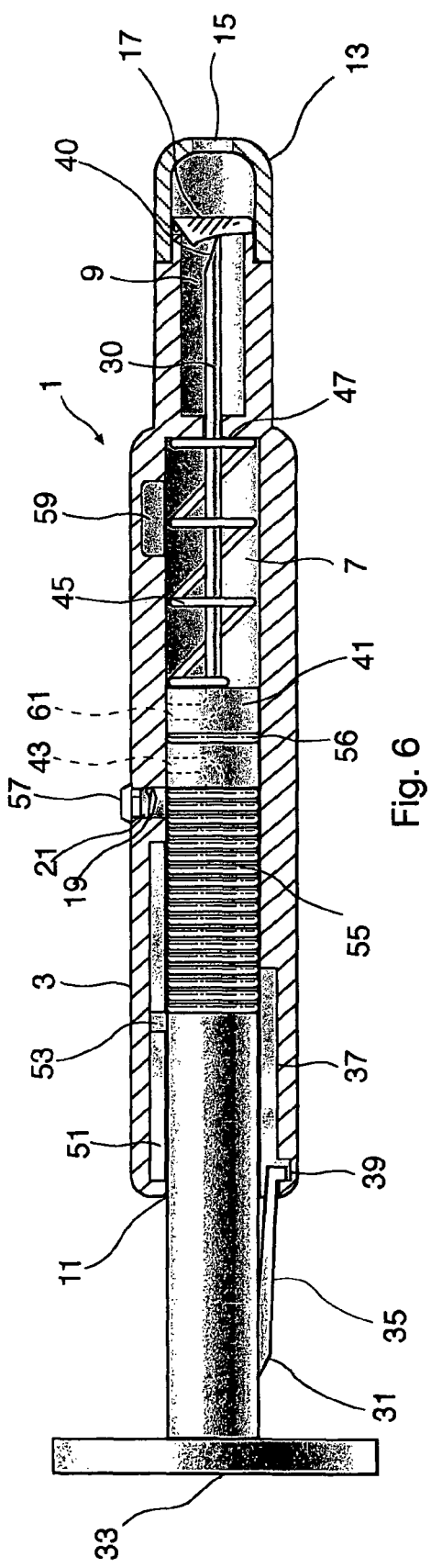
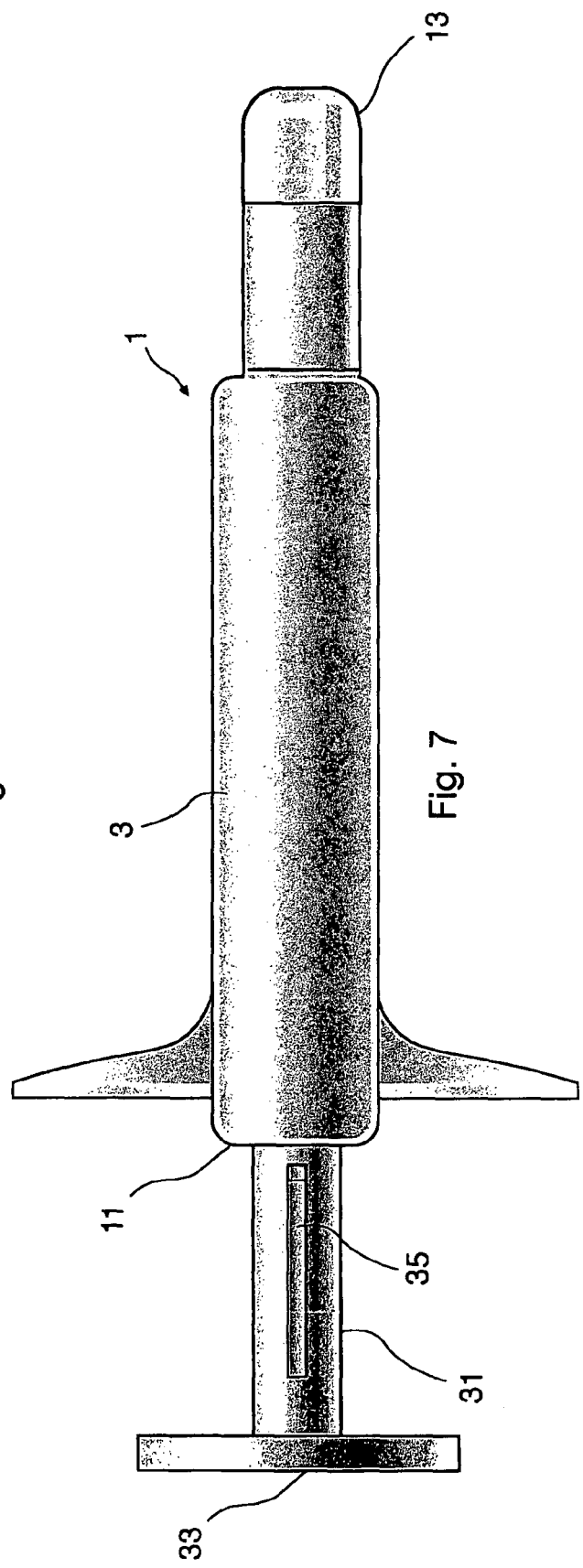

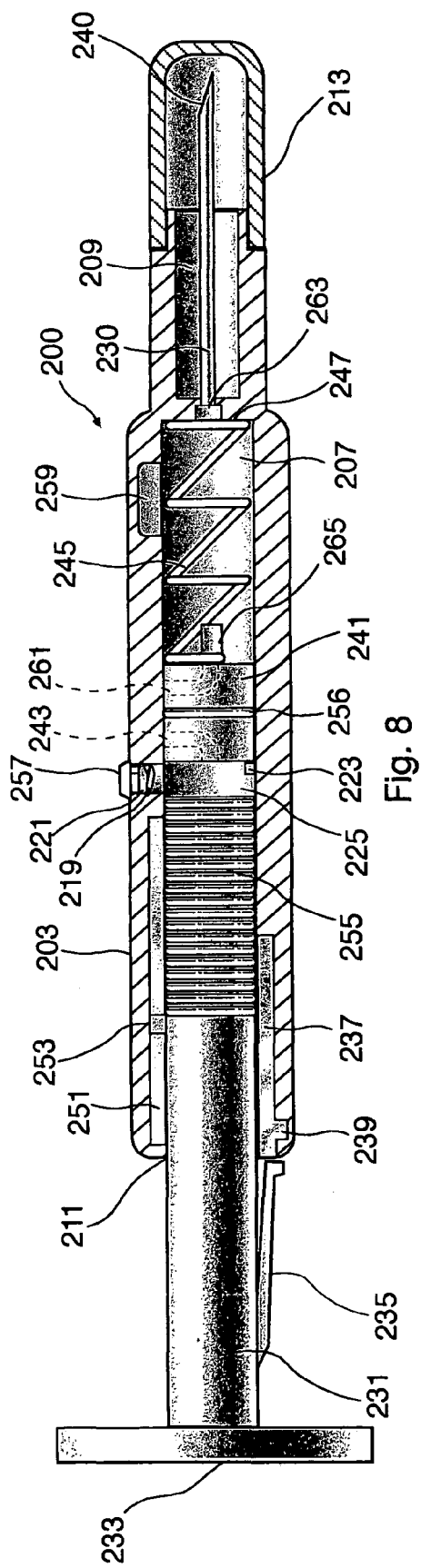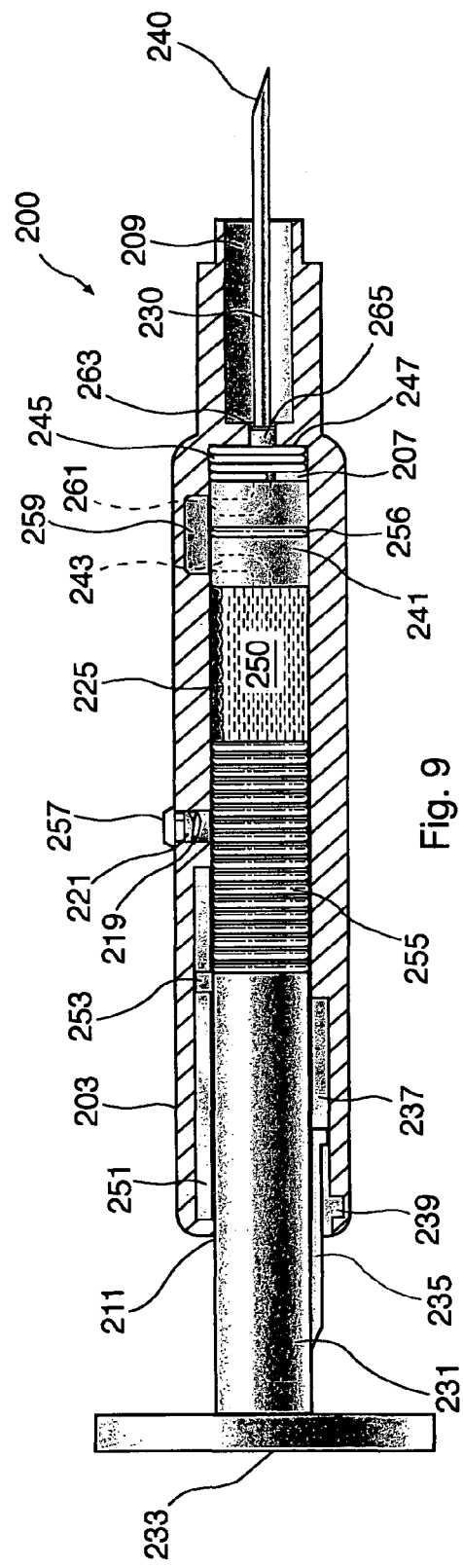

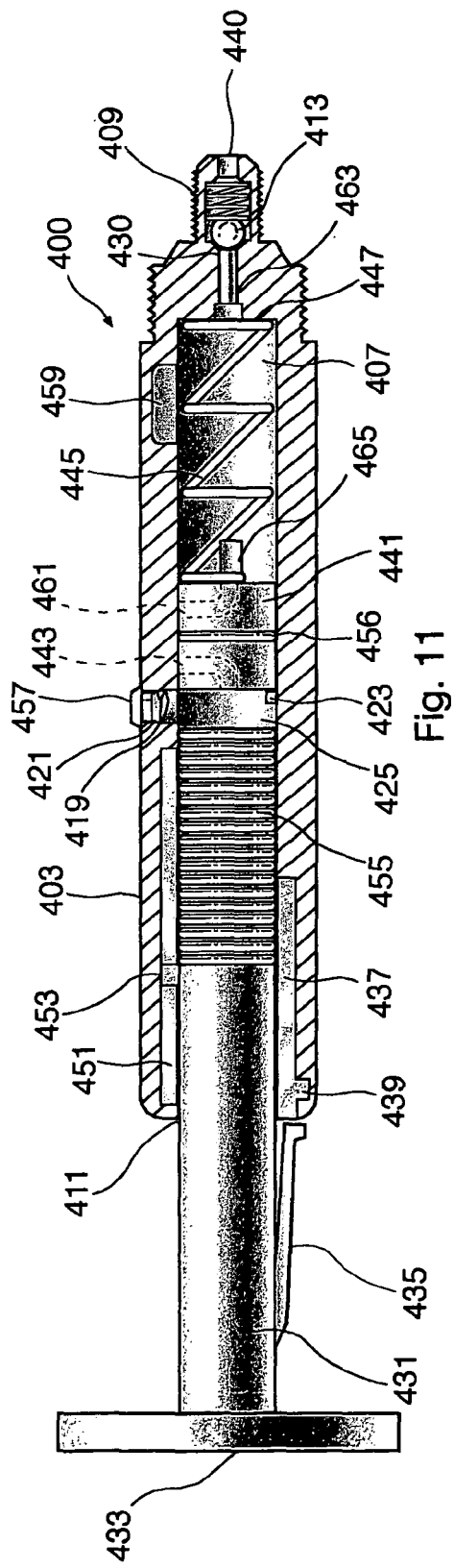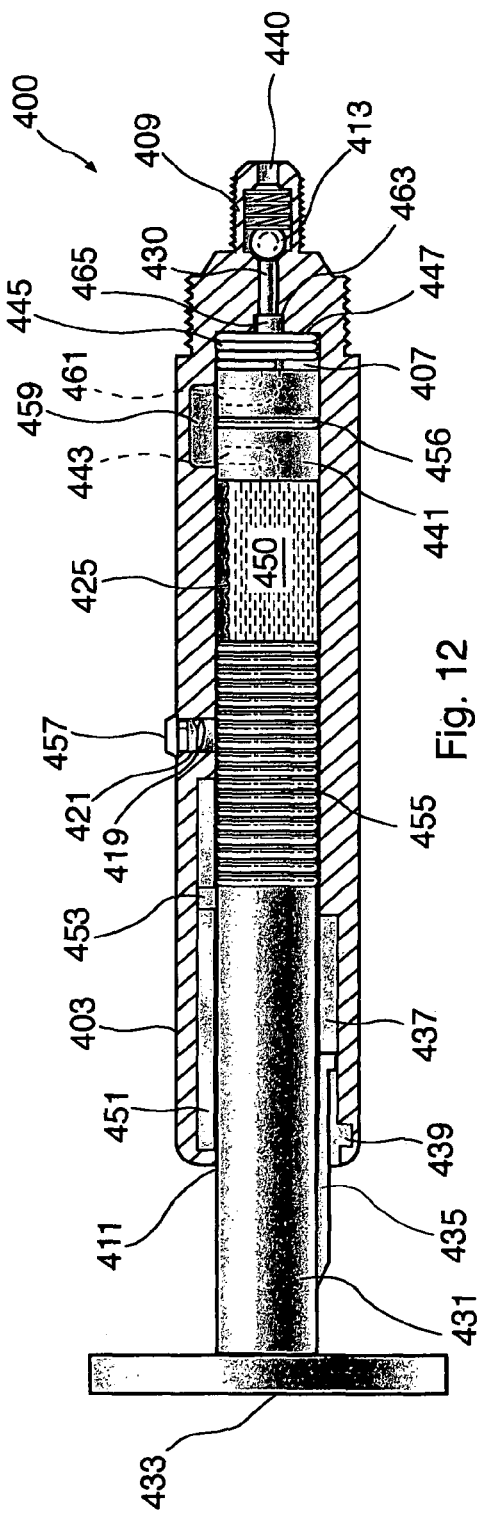

DRUG DELIVERY DEVICE AND METHODOLOGY

BACKGROUND OF INVENTION a. Field of Invention

The invention relates generally to drug delivery devices and methodologies for direct (needle) or indirect (e.g., intravernous) delivery of medication to a patient.

b. Description of Related Art

The following patents relate to the field of drug delivery devices:

U.S. Pat. No. 3,542,023 describes a two-compartment device for the administration of medicaments which is particularly adapted for containing a dry or lyophilized product and the diluent therefor in separate compartments until it is desired to administer the medicament whereupon the dry material and the liquid material may be readily mixed. The device includes a hypodermic syringe barrel having an open end and a closed end, a boss extending from said closed end, a needle affixed to the boss, means for enclosing medicament associated with the barrel, a tubular needle cover, one end of the needle cover sealing the boss, the other end containing an opening therein coaxial with said needle, received in said opening a medicament vial, said medicament vial having an open end and a closed end, received in the open end of said medicament vial a resilient imperforate stopper, said stopper being adapted to be punctured by the open end of said needle to permit the transfer of the contents of said medicament vial to the medicament container associated with said barrel and vice versa.

U.S. Pat. No. 3,980,083 to Elliott describes an infusor unit for dispensing a medicament by injection including a vial having an open end and a closed end and a resilient piston adapted to be initially partially inserted into said vial. The piston having a central through bore which is sealed by a transverse diaphragm and a chamber formed at one end of the piston by the diaphragm and a reduced entryway at its open end to define internal shoulder means. A substantially rigid hollow tubular infusor means which includes means for securing a sharpened cannula which extends outwardly from one end and in communication with the transparent interior of said infusor. The opposite end of the infusor having hollow means for sealing engagement with the piston bore for preassembly and, subsequently, to cooperatively penetrate said diaphragm to provide access of the hollow infusor and its connected passageway with the cannula to the interior of the piston sealed vial.

U.S. Pat. No. 4,592,745 describes a dispenser characterized by provision for use of a replaceable needle and a prefilled cartridge. The dispenser comprises an elongated body separable into two body sections, with the front end section adapted to contain a prefilled cartridge and with provision at the front end for mounting a needle removably thereon. The back end section contains the operating mechanism shown by FIG. 10 to convert the longitudinal movement of a pushable element into unidirectionally rotary movement, then into longitudinal movement of a piston rod that acts to expel fluid through the needle. A multipurpose cap is protective of the needle end when mounted on the front end, and is an operating member when mounted on the rear end, as is illustrated by FIGS. 1 and 2.

U.S. Pat. No. 4,861,335 to Reynolds describes a syringe which provides for the isolated storage of two components of a medicament until immediately prior to use of the syringe. One liquid component is stored in a collapsible chamber of a sealed capsule within a hollow plunger stem of the syringe, and the other component beneath the head of the plunger. A double headed needle arrangement between the head and stem of the plunger is caused to penetrate the plunger head and the capsule when the syringe is to be used so that the plunger may be drawn back to exhaust the contents of the capsule chamber into admixture with the component stored beneath the head of the plunger. Communication through the double headed needle arrangement is then interrupted before the plunger is used to eject the syringe contents through an external needle fitted to the syringe.

U.S. Pat. No. 4,886,495 to Reynolds describes a prefilled syringe for one or two component medicaments is based upon the use of a vial containing a medicament or one component of a medicament, the vial having an open bottom closed by a piston. When the piston is coupled with a plunger, and an adapter cap having an internal needle and an external connection for a needle is placed over a cap of the vial, the latter is converted into a prefilled syringe. The piston has an axial passage closed by a resealable septum, so that a separate diluent stored in a flexible capsule may be introduced into the vial through the piston by a double ended needle mounted on a further cap applied to the capsule, the further cap being coupled within the tubular interior of the plunger so that the double ended needle penetrates the septum in the piston. The capsule is pushed forward onto the double ended needle when its contents are to be expelled into the vial. The capsule and its cap are then removed and discarded.

U.S. Pat. No. 4,915,689 to Theeuwes describes a parenteral delivery system for delivering a beneficial agent. The delivery system comprises a reservoir containing a medical fluid, a vial containing a beneficial solid agent, and a manifold for establishing fluid communication between the reservoir and the vial.

U.S. Pat. No. 4,994,029 to Rohrbough describes a syringe mixer and injector device formed of an injector and an adaptor having opposed interconnectable nozzles, e.g. with mating luer lock connectors, on their facing ends and sockets in their remote ends. Each of the injector and adapter has a protected fluid pathway flow connecting its nozzle and socket, a guideway to receive at its remote end for movement thereon a medicament vial when the vial stopper is connected to its socket, and a recessed short tubular spike forming the pathway portion in its socket and protruding into the socket and terminating inwardly from its remote end sufficiently to protect the spike from unintended human contact and arranged to penetrate the stopper thereat to flow connect its vial with its pathway in protected condition. After charging the injector connected vial with the contents of the adapter connected vial, e.g. by one-way transfer thereto, the injector nozzle may be disconnected from the adapter nozzle and connected directly without modification to a dispensing device having a like nozzle to that of the adaptor. Each of the injector and adapter may be made of plastic as an integral one-piece member.

U.S. Pat. No. 5,069,670 to Vetter et al. describes a hypodermic syringe having a generally cylindrically tubular body extending along an axis and having an axial front end formed with a radially outwardly projecting annular bead, a piston axially displaceable in the body, a plug having a rearwardly directed flange fitting complementarily over the front end of the body at the bead and forwardly blocking the body, and a flat soft seal ring compressed axially between the plug and the front end of the body. The body has a rear end provided with a finger-rest crosspiece and the piston is provided with a plunger projecting axially out the rear end past the crosspiece.

U.S. Pat. No. 5,137,511 to Reynolds describes a prefilled syringe for one or two component medicaments is based upon the use of a vial containing a medicament or one component of a medicament, the vial having an open bottom closed by a piston. When a flexible extension of the piston is coupled with a tubular plunger, and an adaptor cap having an internal needle and an external connection for a needle is placed over a cap of the vial, the latter is converted into a prefilled syringe. The piston may have an axial passage closed by a resealable septum, so that a separate diluent stored in a flexible capsule may be introduced into the vial through the piston by a double ended needle mounted on a further cap applied to the capsule, the further cap being coupled within the tubular interior of the plunger so that the double ended needle penetrates the septum in the piston. The capsule is pushed forward onto the double ended needle when its contents are to expelled into the vial. The capsule and its cap are then removed and discarded. In an alternative arrangement, the cap of the capsule is coupled to the adaptor cap and the diluent introduced into the vial through a closure secured by the cap of the vial, after which the capsule is removed from the plunger and the latter is coupled to the piston.

U.S. Pat. No. 5,281,198 to Haber et al. describes a pharmaceutical component-mixing syringe assembly which is particularly suited for packaging, reconstituting and dispensing a series of equal doses of a multiple component pharmaceutical, such as human growth hormone reconstituted from a diluent component and a lyophilized component. The pharmaceutical components are contained within first and second cartridges of the type having a movable piston. The second cartridge is forced into the interior of the first cartridge causing a spike assembly between the two to fluidly couple the two cartridges and drive the piston of the first cartridge into the first cartridge causing the contents of the first cartridge to be driven into the second cartridge, thereby mixing. A reciprocating ratchet plunger is used to drive the second piston. The distance the ratchet plunger moves, and thus the dose, is determined by the position of a user-inaccessible dosing key stop along the length of the ratchet plunger.

U.S. Pat. No. 5,429,976 to Haber et al. describes a medication dispenser which is used to directly fill a syringe with measured amounts of one or more liquid medications, typically two different types of insulin, from containers, such as vials and cartridges each having a septum at one end; each cartridge has a pierceable piston at the other end. The septum of each container is pierced by hollow liquid spikes while hollow gas spikes pierce the septum of the vial and the piston of the cartridge. Liquid is pumped out of the container and air is replaced into the container through the liquid and gas spikes. Two of the cartridges can contain a diluent and a lyophilized component respectively; the diluent in the first cartridge can be pumped into the second cartridge through a one-way valve to create a mixed pharmaceutical which is then pumped into the syringe, with or without another pharmaceutical.

U.S. Pat. No. 5,466,220 to Brenneman describes a drug vial mixing and transfer device having a piercing connector or a syringe attached to the end of one or more ports with interconnecting fluid passageways. Further, the piercing connector is used to support and penetrate standard glass drug vials filled with powder or lyophilized drugs or liquid diluent, while the syringe is used to transfer liquid diluent and drug solutions between the vials and the syringe advantageously within a sealed system.

U.S. Pat. No. 5,478,316 describes a device for automatically injecting a material into the body. The device includes a drive assembly and a syringe assembly which is mounted to the drive assembly. The drive assembly includes a drive rod, a driver releasably coupled to the drive rod, and a constant force spring which urges the drive rod towards the syringe assembly. The spring first urges the coupled drive rod and driver along the axis of the device, causing the skin to be penetrated by the needle of the syringe assembly. The drive rod is then decoupled from the driver. The spring continues to urge the drive rod in the axial direction, whereby the drive rod engages a piston in the syringe assembly and causes the displacement of the material therein.

U.S. Pat. No. 5,554,125 to Reynolds describes a prefilled syringe for one or two component medicaments which is based upon the use of a vial containing a medicament or one component of a medicament, the vial having an open bottom closed by a piston. When a flexible extension of the piston is coupled with a tubular plunger, and an adaptor cap having an internal needle and an external connection for a needle is placed over a cap of the vial, the latter is converted into a prefilled syringe. The open bottom of the vial is configured so as not to interfere with handling of the vials by conventional vial sterilizing, filling and capping machinery, and may not be formed so as to provide an internal shoulder which will secure a piston retention member.

U.S. Pat. No. 5,673,094 describes a syringe for injecting multiple sequential dosages of a liquid medicine and includes a single actuator for initiating a penetration and injection sequence. The syringe hereof is adjustable for different dosages while providing for physical selection of a desired, predetermined dosage. The syringe includes a retraction mechanism for withdrawing the needle into a protective collar after administration of the dosage. The syringe receives a vial for administering multiple dosages without the necessity of replacing the vial after each administration.

U.S. Pat. No. 6,030,363 describes an injectable medicament dispenser for use in controllably dispensing fluid medicaments such as insulin, antibiotics, oncolytics and the like from a prefilled container at a uniform rate. The dispenser includes a unique stored energy source in the form of a compressively deformable, polymeric elastomeric member that provides the force necessary to controllably discharge the medicament from the prefilled container which is housed within the body of the device. After having been deformed, the polymeric, elastomeric member will return to its starting configuration in a highly predictable manner.

U.S. Pat. No. 6,221,041 B1 to Russo describes a fluid transfer device connecting a medical vessel and an intravenous bag for enabling the mixing in closed system of the two products contained therein by means of a syringe, comprising a three-way plug valve assembly with a first port ending in a connector for a syringe, and a second and a third port, each one provided into a respective spike connected to a housing for a container of medicinal product. Within the first one of the said two spikes a further independent channel is provided for the inlet and the outlet of air, communicating with the external environment through a hydrophobic filter. The second one of the said two spikes is capable of piercing the rubber closure of the injection point of a bag of medicinal product, and the corresponding housing consists of two flexible arms fastenable to each other at the respective ends, so as to be tightened around the tube of the said injection point.

U.S. Pat. No. 6,599,268 B1 describes a syringe that has a retractable needle and a barrel having an open proximal end and an open distal end defining a receiver with an inward shoulder. The barrel has a hollow bore, an elongate plunger with a proximal end and a distal open end with a cavity within. A stopper occludes the open end of the cavity. The syringe has an elongate hub with a proximal flange. The hub is within and sized for slideable movement within the receiver at the distal end of the barrel with the flange defining a distal end of a chamber. There is a sleeve sized to fit with a clearance about the hub disposed between the shoulder and the flange when the hub is in the receiver, the sleeve having a sharpened proximal end and a proximal end connected to the passageway of the hub with the pointed end of the needle extending outwardly. There is a spring disposed about the hub compressed to provide a bias between the receiver and the flange so that when a force greater than required to expel fluid from the chamber is applied, the plunger causes the cutting surface to cut through the flange and stopper and expose the cavity to allow the spring to urge the hub into the cavity in the plunger and retract the needle to a position within the syringe.

U.S. Pat. No. 6,632,198, B2 describes a retracting needle assembly for use with a syringe barrel having a cylindrical collar and a plunger having a release element with a sharp distal end includes an outer hub having a passageway therethrough and an inner hub having a proximal end, a distal end and a conduit therethrough. The proximal end of the inner hub has an inner portion and a dissociable outer portion connected to the inner portion. The dissociable outer portion is further connected to the outer hub. The distal end of the inner hub is smaller than the passageway of the outer hub at the distal end of the outer hub and projects distally outwardly therefrom. A needle channel having a distal end, a proximal end, and a lumen therethrough is connected to the inner hub so that the lumen is in fluid communication with the conduit. An energized spring is contained between the inner and outer hub. Structure is provided for connecting the outer hub to the collar of the syringe barrel.

U.S. Pat. No. 6,645,181 B1 describes a drug delivery device for mixing and delivering a drug by injection. The device includes a housing having a first port or opening therein that receives a first container that contains a fluid or powdered drug, for example a lyophilized drug. The housing can also include a second port or opening that receives a second container that contains a fluid to be mixed with the drug to form an injectable fluid. The device includes a manifold having a channel that fluidly connects the first and second containers. A penetration membrane such as a needle is used to inject the drug into a patient which is in fluid communication with the first container. The needle is moveable from a storage position in the housing to an injection position extending through the housing.

U.S. Pat. No. 6,652,483 B2 describes a device for providing medication for injection by a jet injector includes a cassette which connects an injector system to a reservoir. The cassette forms a fluid pathway at an interface of a cassette lower body and a cassette upper body. The cassette also forms an impulse chamber with a nozzle leading therefrom. The fluid pathway interconnects the reservoir with the impulse chamber. The medication flows from the reservoir along the fluid pathway and into the impulse chamber. Force from an impulse generator drives the fluid medicament from the impulse chamber through the nozzle, out an orifice in a tip of the nozzle, and into the skin of a patient. To prevent the pressure waves generated by the jet injector from breaking a glass cartridge in the reservoir, the fluid pathway is blocked, using a series of right angles or valves.

U.S. Pat. No. 6,669,671 B1 describes a retractable syringe needle comprising a needle assembly including: a needle-holding mechanism comprising a hub and an annular sleeve connected with said hub; a hypodermic needle extending through said hub; and a pin directly connected to the exterior surface of said annular sleeve; a container having a tubular wall with a longitudinal slot therein, said container having a first open end adapted to receive a syringe barrel and a second open end adapted to admit a syringe needle, said container having said needle assembly mounted therein so that the pin is slideably engaged by the longitudinal slot, so that said needle assembly may be moved from a first position where the needle is within the container to a second position where the needle is exposed by sliding the pin toward the second open end of the container and causing the needle to pass though the second open end; a means for biasing the needle assembly toward said first position; and means for releasably engaging the pin at a defined location in said longitudinal slot so as to hold said needle assembly in said second position; wherein said means for releasably engaging the pin comprises a notch which intersects said longitudinal slot at said defined location, so that said needle assembly may be releasably held in said second position by sliding said pin out of said longitudinal slot into said notch.

U.S. Pat. No. 6,676,641 B2 describes a hypodermic syringe that includes a barrel with a plunger assembly slideably extending therein. The plunger assembly includes an outer plunger and an inner plunger telescoping together with a bungee in tension. A seal stop is located at the seal end of the plunger assembly and holds an annular seal in radial extension sealing against the internal sidewall of the barrel. A luer hub assembly is fixed at the needle end of the barrel. A plunger cap may be advanced after injection to rotate the plunger assembly. Such rotation engages a probe on the end of the plunger assembly with the luer hub, disengages the seal stop to release the annular seal, engages the seal stop with the luer plunger assembly causing release of the luer hub assembly from the barrel and releases the engagement between the outer plunger and inner plunger. The foregoing provides for the retraction of the luer hub and associated needle into the barrel.

U.S. Pat. No. 6,685,677 B2 describes a needle assembly withdraws medicine from a vial having a rubber septum and injects the medicine into a port in a patient while not endangering the caregiver with an accidental stick with a contaminated used needle. The needle assembly includes a sharp hollow needle for penetrating a septum of a vial and a blunt cannula for injecting into an injection port. The needle can be of any type including intramuscular. The blunt cannula concentrically surrounding the sharp hollow needle, and extends relative to the sharp hollow needle in a locked position.

U.S. Pat. No. 6,706,031 B2 describes a needleless access system adapted to be mounted on a vial comprising a generally elongated tubular housing having an interior dividing wall, flexible hooks projecting upwardly from the dividing wall which are diametrically opposed, a pair of confronting splines projecting upwardly from the interior dividing wall, a hub insert having a piercing tip normally supported in an armed position by hook elements, a series of outwardly projecting teeth which engage and are guided in the splines during axial displacement of the hub insert relative to the splined housing, and said hub insert having means for mounting a syringe assembly whereby the hub insert maybe activated axially guided by the splines so that the piercing tip engages the stopper in a vial aligned therewith.

U.S. Pat. No. 6,752,782 B2 describes an automatically retractable safety syringe includes a needle assembly consisting of a cannula, a needle hub and a rubber O-ring, a needle cap, a retracting spring, a breakable and retractable plunger, a plunger gasket and a medicine barrel; in accordance with the structure of the said automatically retractable safety syringe of the present invention, since the breakable plunger is assembled inside the medicine barrel, after being pushed all the way to the end, it is forced to break automatically into two parts for reducing its length so as to provide enough space for the retracting spring to drive the needle assembly moving along the sliding passages for accomplishing an automatically retracting action.

U.S. Pat. No. 6,776,775 B1 describes a retractable needle assembly for use in medical procedures, comprising a needle assembly including a hub, a hollow needle passing though the hub and projecting from the posterior end of the hub, and a tubular sleeve having a radially directed hole therethrough connected with the anterior end of the hub; a tubular sheath having a wall with a radially directed hole therethrough, wherein the needle assembly is positioned within the tubular sheath so that it may be moved reversibly between an exposed position and a retracted position; a means for reversibly locking the needle assembly in its exposed position; a means for reversibly locking the needle assembly in its retracted position; and a means for permanently locking the needle assembly in its retracted position, said permanent locking means comprising a radially-directed peg mounted on an exterior surface of the tubular sheath so that one end of the radially-directed peg is adapted to be pushed inwardly through the hole in the wall of the tubular sheath and through the hole in the tubular sleeve, wherein said one end of the radially-directed peg may not be withdrawn through the hole in the tubular sleeve after it has been pushed through the hole in the tubular sleeve.

U.S. Pat. No. 6,800,067 B2 describes a safety syringe that includes two major components; a barrel and a plunger; a needle hub engaged with the barrel and a plunger slid ably received in the barrel to engage with the needle hub and to retract the needle into the barrel. A V-shaped groove formed a thin membrane surround the needle hub. The V-shape groove separates the needle hub and the barrel into two peripheries-an inner periphery of the barrel and an outer periphery of the hub. The inner periphery of the barrel and the outer periphery of the hub are thicker then the thin membrane. Multiple pyramidal blocks extended from the outer periphery of the hub facing outward to the barrel. Multiple triangular cutouts with V-shape groove edge defined in the inner periphery of the barrel respectively correspond to one of the multiple pyramidal blocks.

U.S. Pat. No. 6,846,301 B2 describes a safety syringe includes a generally tubular body having a needle end and plunger end, needle and retractable needle seat, two-way valve, plunger, stopper, piston, and rear plunger may be moved to create a vacuum in the plunger. The user then moves the plunger toward the needle end, pressurizing a vial, then pulls backward to a selected position corresponding to the desired volume of fluid to be withdrawn. At the conclusion of the injection stroke, the piston is disengaged from the plunger. The vacuum within the plunger retracts the needle safely into the tubular body.

U.S. Pat. No. 6,805,689 B2 describes a blood collector system utilizes a standard disposable needle assembly and standard blood collecting and receiving tubes of the type sealed by a pierceable septum. The system has a hollow cylinder, including an internally apertured sleeve into which the needle assembly is mounted and into which the sealed blood collecting tubes are inserted to be pierced by a needle of the needle assembly. A protective sheath with two clips is concentrically mounted to the barrel cylinder with slot on both sides of the barrel so that the hollow cylinder can move down to cover the patent contacted needle. On both sides of the barrel, there are one upper slot and one lower slot, a slot channel between the upper slot and lower slot. The clip is shaped so that it can snap in the upper and lower slot and can be only slide down from the upper slot to lower slot, but not backwards. After the needle is taken out from a patient, the clip will be pushed down out of the upper slot, then slide down through the slot channel, then be pushed down to snap in the low slot of the barrel in order to cover the used needle from a patient. The apparatus of the invention eliminates the health care worker's exposure to accidental needle pricks.

U.S. Pat. No. 6,863,659 B2 describes a sharp safe hydraulic retractable syringe that is supplied with a hypodermic needle fully housed within an elongated hollow barrel which cannot be used until the plunger rod stop has been removed and the plunger rod has been pushed into the loading position to receive the required liquid into the elongated hollow barrel. The hydraulic retractable syringe assembly is preceded by a retractable mechanism is contained by a three-legged retaining clip to hold twin conical helical shape springs separated by a spring separation plate within two spring retaining cups. Twin conical shape springs are released by the hydraulic pressure exerted by the liquid onto the activating ring with three molded pistons which passes through a sealing member and exerts axial pressure onto the three release sides to introduce radial pressure onto the three-legged clip to release the conical spring pressure placed onto two spring retaining cups causing the twin conical helical shape springs to be set apart and retract up into the elongated hollow barrel. The three-legged retaining clip has two of its three legs preset so as to force the spring separating plate against the hypodermic needle causing the hypodermic needle to misalign and thereby rendering the sharp safe hydraulic retractable syringe non-functional for reuse. This invention can be incorporated into any syringe.

U.S. Pat. No. 6,872,190 B1 describes a syringe that comprises a body forming a liquid reservoir, carrying a needle for injecting the liquid, and having a plunger movably mounted in the body. The body is housed in a safety sheath to be axially movable between an active position in which the needle projects through a distal end of the sheath and a protection position in which the needle is retracted inside the sheath and towards which position the body is urged resiliently. The body is prevented from moving relative to the sheath in the active position by locking means that opposite the resilient force on the body, and that are releasable by means which are activated when the plunger is in an end-of-liquid-injection position.

U.S. Pat. No. 6,926,696 B2 describes a retractable needle assembly for use in medical procedures comprising a needle assembly including a hub, a hollow needle passing through the hub and projecting from the posterior end of the hub. A tubular sheath having a longitudinal slot extending along a portion of its length. A post attached to the hub and positioned to project through said longitudinal slot such that the needle and hub assembly may slide along the length of the sheath from a position exposing said needle to a retracted position, a means for reversibly locking the needle in the exposed position and means for permanently locking the needle in the retracted position both reversibly or permanently are disclosed. Ivan U.S. Pat. No. 7,025,389 B2 describes a method and device for facilitating fluid communication between a sealed container having an access port and at least one fluid passageway. The device includes a connector provided with a body that defines a fluid passageway between first and second ends of the body. The first end of the body is configured for receiving the fluid source, and the second end is configured for receiving an access port of the container. A locking member is associated with the body and prevents movement of the body relative to the access port with the locking member is in a locked position. The device scan be used for the transfer of cytotoxic or other drugs (i.e., fluids) to the container and may remain attached to the access port and used to administer a drug from the container to a patient by means of an administration set with a male luer connector.

Notwithstanding the foregoing prior art patents, the present invention is neither taught nor rendered obvious in view of said prior art references.

SUMMARY OF INVENTION

The invention solves the problems and overcomes the drawbacks and deficiencies of prior art drug delivery systems by providing relatively simple mechanisms that are based on simple push and pull movements, but contain automatic valving and resealing features to prevent unintentional or accidental expose or release of potentially toxic or otherwise harmful medications.

Thus, the present invention drug delivery device, which includes: (a.) a main housing having a shaft with a proximal end and a distal end, having a drug holding reservoir within the shaft, and having a drug release conduit located in the shaft toward the distal end, and having an outlet located at the distal end of the shaft; (b.) a fill port with an optional one way valve, the fill port being connected to an inlet conduit; (c.) the inlet conduit connected to the shaft at the holding reservoir; (d.) a one-way valve located within the inlet conduit between the piercing element and the holding reservoir positioned to permit flow from the drug vial receiving member to the holding reservoir and not the opposite; (e.) a slide valve having a distal end and a proximal end, and being located in the shaft and adapted for movement within the shaft from a first position to a second position and vice versa, wherein when the slide valve is in the first position, the drug holding reservoir is closed from the drug release conduit, and when the slide valve is in the second position, the drug release conduit is open to permit liquid drug to pass through the slide valve from the drug holding reservoir, the slide valve having a first wall facing toward the holding reservoir and an opposing second wall facing away from the holding reservoir, and the first wall has a liquid inlet channel connecting to the side wall and the second wall has a liquid outlet channel are in proximity to one another and not directly connected to one another; (f.) a needle functionally connected to the valve outlet at its distal end to the slide valve; (g.) a plunger being partially and slideably located in the proximal end of the shaft, the plunger having sufficient length to be moved from a first plunger position to a second plunger position, and vice versa; (h.) a spring located in the shaft at the distal end of the slide valve biasing the slide valve to its first position; wherein, when the drug fill port is connected to a liquid drug source, such as a feed line or a vial or other package, and the plunger is moved from the first position to the second position, the liquid drug will be moved from its source into the fill port, and through the optional one-way valve, if there is one, and through the inlet conduit into the drug holding reservoir, and when the plunger is moved from its second position toward its first position, the first spring will compress and the slide valve will move from its closed, first position to its open, second position in alignment with the drug release conduit, and when the plunger is moved from its second position to its third position, the first spring remains compressed and the second spring will compress and the side arm of the plunger will advance the rod and the piston to move drug through the drug outlet conduit, through the valve and through the needle for injection thereof.

In some preferred embodiments of the present invention drug delivery device, the slide valve includes a valve conduit that connects from the drug release conduit to the needle when the slide valve is in its second position.

In some preferred embodiments of the present invention drug delivery device, the needle is directly connected to the slide valve and travels with the slide valve from its first position to its second position and vice versa.

In some preferred embodiments of the present invention drug delivery device, when the slide valve is in its first position, the needle is fully contained within the shaft, and when the slide valve is in its second position, the needle is partially extended beyond the distal end of the shaft so as to be positioned for injection.

In some preferred embodiments of the present invention drug delivery device, the distal end of the shaft includes a gate that is closed when in its rest position when the needle is fully contained within the shaft and opens when the valve and needle are moved from the first position to the second position and the needle is partially extended.

In some preferred embodiments of the present invention drug delivery device, the device further includes a child resistant mechanism on at least one of the shaft and the plunger, that has a lock position to prohibit movement of the slide valve from the first position to the second position and a go position and the child resistant mechanism must be engaged into the go position from the lock position to permit movement of the plunger to move the slide valve form the first position to the second position.

In some preferred embodiments of the present invention drug delivery device, the needle is physically separate from the slide valve and is stationary relative to the shaft.

In some preferred embodiments of the present invention drug delivery device, the device includes a catch mechanism to prevent removal of the plunger from the shaft once it is positioned therein.

In some preferred embodiments of the present invention drug delivery device, the main housing includes a keyway for slide valve to position siad slide valve channels in bias with the drug release conduit of the main housing.

In some preferred embodiments of the present invention drug delivery device, the main housing is comprised of at least two assembled sections for ease of manufacture. These may be the main housing section that houses the initial fill, the plunger and valve mechanisms., and a separate nose cone section that may include an internal and/or an external valve, a fixed needle or orifice for a moving needle, an IV or other port connector, etc. These two sections may be connected by any know technique, such as heat welding, physical bonding, force fitting with interlock features, etc.

In some preferred embodiments of the present invention drug delivery device, the drug delivery device includes: (a.) a main housing having a shaft with a proximal end and a distal end, having a drug holding reservoir within the shaft, and having a drug release conduit located in the shaft toward the distal end, and having an outlet located at the distal end of the shaft; (b.) a fill port with an optional one way valve, the fill port being connected to an inlet conduit; (c.) the inlet conduit connected to the shaft at the holding reservoir; (d.) a one-way valve located within the inlet conduit between the piercing element and the holding reservoir positioned to permit flow from the drug vial receiving member to the holding reservoir and not the opposite; (e.) a slide valve having a distal end and a proximal end, and being located in the shaft and adapted for movement within the shaft from a first position to a second position and vice versa, wherein when the slide valve is in the first position, the drug holding reservoir is closed from the drug release conduit, and when the slide valve is in the second position, the drug release conduit is open to permit liquid drug to pass through the slide valve from the drug holding reservoir, the slide valve having a first wall facing toward the holding reservoir and an opposing second wall facing away from the holding reservoir, and the first wall has a liquid inlet channel connecting to the side wall and the second wall has a liquid outlet channel are in proximity to one another and not directly connected to one another; (f.) a needle functionally connected to the valve outlet at its distal end to the slide valve; (g.) a plunger being partially and slideably located in the proximal end of the shaft, the plunger having sufficient length to be moved from a first plunger position to a second plunger position, and vice versa; (h.) a spring located in the shaft at the distal end of the slide valve biasing the slide valve to its first position; wherein, when the drug fill port is connected to a liquid drug source, such as a feed line or a vial or other package, and the plunger is moved from the first position to the second position, the liquid drug will be moved from its source into the fill port, and through the optional one-way valve, if there is one, and through the inlet conduit into the drug holding reservoir, and when the plunger is moved from its second position toward its first position, the first spring will compress and the slide valve will move from its closed, first position to its open, second position in alignment with the drug release conduit, and when the plunger is moved from its second position to its third position, the first spring remains compressed and the second spring will compress and the side arm of the plunger will advance the rod and the piston to move drug through the drug outlet conduit, through the valve and through the needle for injection thereof.

In some preferred embodiments of the present invention drug delivery device, the slide valve includes a valve conduit that connects from the drug release conduit to the needle when the slide valve is in its second position.

In some preferred embodiments of the present invention drug delivery device, the needle is directly connected to the slide valve and travels with the slide valve from its first position to its second position and vice versa.

In some preferred embodiments of the present invention drug delivery device, when the slide valve is in its first position, the needle is fully contained within the shaft, and when the slide valve is in its second position, the needle is partially extended beyond the distal end of the shaft so as to be positioned for injection.

In some preferred embodiments of the present invention drug delivery device, the distal end of the shaft includes a gate that is closed when in its rest position when the needle is fully contained within the shaft and opens when the valve and needle are moved from the first position to the second position and the needle is partially extended.

In some preferred embodiments of the present invention drug delivery device, the device further includes a child resistant mechanism on at least one of the shaft and the plunger, that has a lock position to prohibit movement of the slide valve from the first position to the second position and a go position and the child resistant mechanism must be engaged into the go position from the lock position to permit movement of the plunger to move the slide valve form the first position to the second position.

In some preferred embodiments of the present invention drug delivery device, wherein the needle is physically separate from the slide valve and is stationary relative to the shaft.

In some preferred embodiments of the present invention drug delivery device, the device includes a catch mechanism to prevent removal of the plunger from the shaft once it is positioned therein.

In some preferred embodiments of the present invention drug delivery device, the main housing includes a keyway for slide valve to position siad slide valve channels in bias with the drug release conduit of the main housing.

In some preferred embodiments of the present invention drug delivery device, the main housing is comprised of at least two assembled sections.

The present invention also includes a methodology for drug delivery utilizing a manual drug delivery device, which includes the steps of: A.) loading a drug holding reservoir of a manual drug delivery device with a predetermined amount of a liquid drug and sealing the liquid drug in the drug holding reservoir, the manual drug delivery device including the following structure: (i) a main housing having a shaft with a proximal end and a distal end, and having the drug holding reservoir separate from the shaft, and having a drug outlet conduit connected from the drug holding reservoir to the shaft; (ii) fill means on the main housing for loading a drug into the drug holding reservoir, the fill means including opening and closing means and a one way valve to permit the medication to enter but not exit the fill port; (iii) a piston with a drive rod, the piston being slideably located within the reservoir; (iv) a slide valve having a distal end and a proximal end, and being located in the shaft and adapted for movement within the shaft from a first position to a second position and vice versa, wherein when the slide valve is in the first position, the drug outlet conduit is closed from the shaft, and when the slide valve is in the second position, the drug outlet conduit is open to permit liquid drug to pass through the slide valve; (v) a needle functionally connected at its distal end to the slide valve; (vi) a plunger having a side arm, the plunger being partially and slideably located in the proximal end of the shaft, the side arm being in alignment with the rod, the plunger having sufficient length to be moved from a first plunger position, being a rest position, to a second plunger position, being a slide valve open position, and from the second position to a third position, being an injection position; (vii) a first spring located in the shaft at the distal end of the slide valve, and a second spring located in the shaft at the proximal end of the slide valve between the plunger and the slide valve, the first spring being weaker than the second spring so as to yield and compress fully before the second spring compresses; B.) positioning the device adjacent a drug injection receiver; C.) moving the plunger into the shaft from the first position to the second position, so as to compress the first spring and so as to move the slide valve from its closed, first position to its open, second position in alignment with the drug outlet conduit; D.) moving the plunger from its second position to its third position, while the first spring remains compressed, and so as to compress the second spring and advance the side arm of the plunger to act upon the rod and the piston to move the drug through the drug outlet conduit, through the valve and through the needle to inject the drug into the injection receiver.

In some preferred embodiments of the present invention drug delivery methodology, the slide valve includes a valve conduit that connects from the drug outlet conduit to the needle when the slide valve is in its second position so as to permit the drug to flow therethrough.

In some preferred embodiments of the present invention drug delivery methodology, the needle is directly connected to the side valve and travels with the slide valve from its first position to its second position and vice versa when the step C. is effectuated.

In some preferred embodiments of the present invention drug delivery methodology, when the slide valve is in its first position, the needle is fully contained within the shaft, and when the step C. is effectuated, the slide valve is moved to its second position and the needle is partially extended beyond the distal end of the shaft so as to be positioned for injection.

In some preferred embodiments of the present invention drug delivery methodology, the distal end of the shaft includes a gate that is closed when in its rest position when the needle is fully contained within the shaft and opens when step C. is effectuated, the valve and needle are moved from the first position to the second position and the needle is partially extended.

In some preferred embodiments of the present invention drug delivery methodology, the device further includes a child resistant mechanism that has a lock position to prohibit movement of the slide valve from the first position to the second position and a go position and the methodology includes the step of engaging the child resistant mechanism by moving it into the go position from the lock position to permit movement of the slide valve form the first position to the second position.

In some preferred embodiments of the present invention drug delivery methodology, the needle is physically separate from the slide valve and is stationary relative to the shaft.

In some preferred embodiments of the present invention drug delivery methodology, wherein the device includes a catch mechanism to prevent removal of the plunger from the shaft once it is positioned therein.

In some preferred embodiments of the present invention drug delivery methodology, the main housing includes a runway for the side arm and the arm includes a catch that fits into the runway such that when the plunger is partially positioned within the shaft, the catch inhibits removal of the plunger from the shaft.

In some preferred embodiments of the present invention drug delivery methodology, the drug delivery methodology further includes the step of releasing the plunger so that the first spring and second spring are uncompressed and the slide valve returns to its first position.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings:

FIGS. 1a, 1b, 1c and 1d illustrate various steps in the functionality of one preferred embodiment of the present invention drug delivery device and methodology, and block diagram format;

FIGS. 2, 3, 4, 5 and 6 show side cut views of one preferred embodiment of a present invention drug delivery device with sliding valve and needle in various stages of use;

FIG. 7 shows a full side view of the present invention device shown in FIGS. 2 through 6 above;

FIGS. 8 and 9 show side cut views of an alternative embodiment present invention drug delivery device with a stationary needle;

FIGS. 11 and 12 show side cut views of another present invention embodiment of a drug delivery device for connection to an intervenes feed system; and, FIGS. 13 and 14 illustrate side cut views of another present invention drug delivery device similar to that shown in FIGS. 11 and 12 above, but with an additional safety feature and flap valve.

DETAILED DESCRIPTION OF THE EMBODIMENTS

Figures 10A, 10B, 10C, 10D:
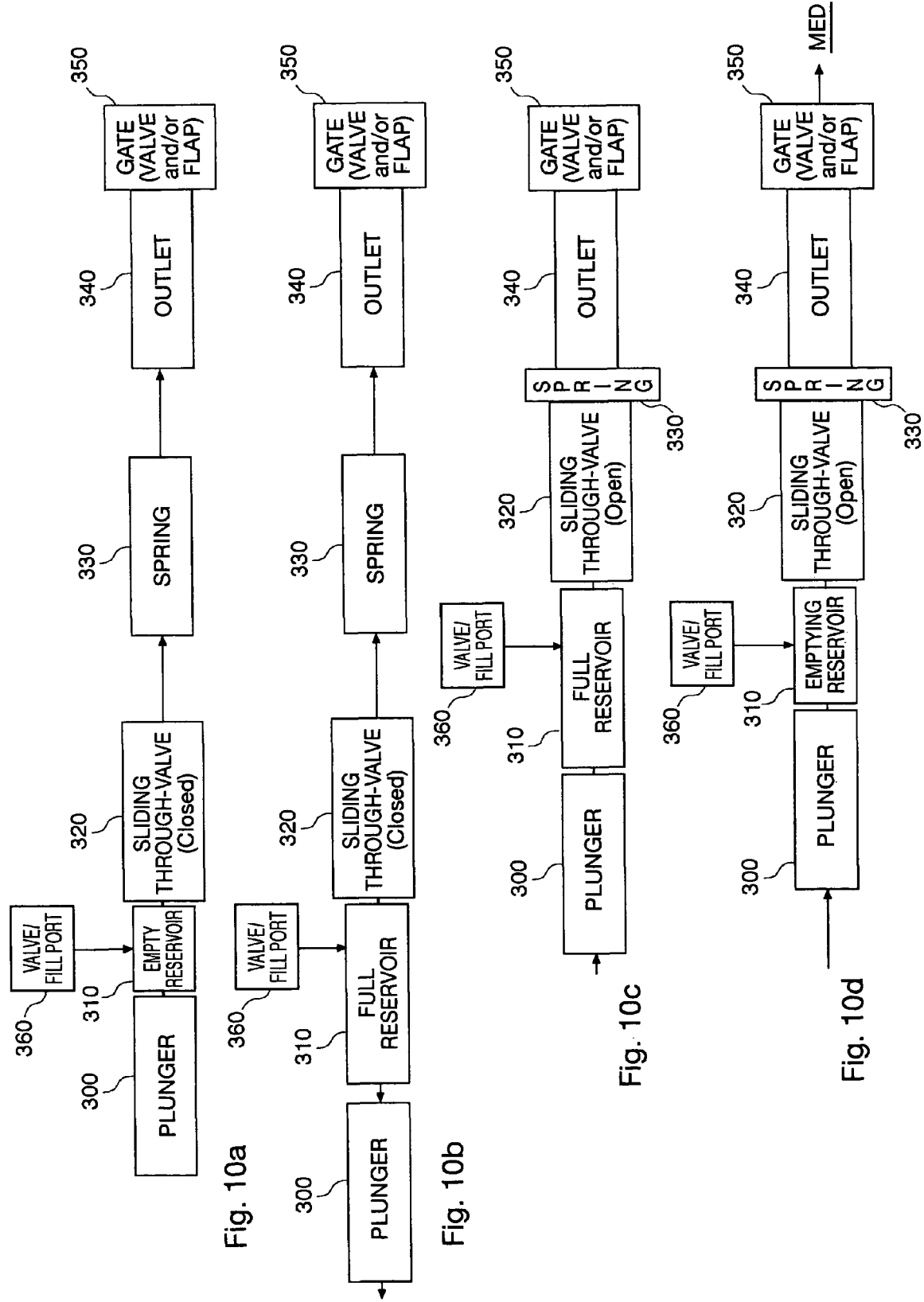
FIGS. 10a, 10b, 10c and 10d show various steps in the functionality of one preferred embodiment of the present invention drug delivery device and methodology, and block diagram format.

Referring now to the drawings, like reference numerals designate corresponding parts throughout the several views that present the same embodiment.

FIG. 1a through FIG. 1d illustrate various stages in the functionality and the methodology of utilization of the present invention drug delivery devices in block diagram format. The external housing of the device is excluded for simplicity, but may be any functional housing, from a syringe type device to a table model instrument, without exceeding the scope of the invention. In FIG. 1a, plunger 100 is positioned in a housing (not shown) adjacent empty reservoir 110, also encompassed by said housing. Connected to the empty reservoir 110 through the housing is a fill port 160 with opening and closing means and a one way incoming valve to prevent liquid exit through port 160. On the opposite side of reservoir 110 from plunger 100 is sliding through-valve 120. Spring 130 pushes valve 120 to the left to maintain valve 120 closed when no pressure is exerted upon it. Gate 150 is generally closed, unless opened manually or opened by needle 140 being pushed against it. Needle 140 passes through spring 130 and is connected directly to the valve 120. Thus, when valve 120 moves, needle 140 moves with it. Identical numbers are used for identical block diagram components in FIGS. 1b, 1c and 1d.

When plunger 100 is pulled to the left (or pushed by a positive pressure inflow), FIG. 1b, the liquid medication from a source, such as a container or feed line, will pass through fill port 160 to reservoir 110 and fill reservoir 110. The one way valve (not shown) prevents liquid med from flowing back into its source or out of the device. When plunger 100 is next pushed to the right toward valve 120, FIG. 1c, the med in full reservoir 110 acts as a moving piston to push against sliding through valve 120 and pushes valve 120 against spring 130 to compress the spring 130 until it stops at an open valve position. Needle 140 has advanced concurrently with valve 120 and has opened or passed through gate 150.

Next, when plunger 100 is pushed further to the right (pushed in further), FIG. 1d, the med in reservoir 110 is moved out of the reservoir 110, through open valve 120 and out needle 140, to deliver the med directly to the patient or otherwise. As soon as the nurse or other user releases the push pressure on plunger 100, the spring 130 automatically pushes the valve 120 back to its closed position, moves the needle back and gate 150 automatically closes. All aspects of the device are sealed to the outside, preventing drips and evaporative losses.

FIGS. 2, 3, 4, 5 and 6 show side cut views, and FIG. 7 shows a side uncut view, of one preferred embodiment of a present invention drug delivery device 1 with a sliding valve and needle in various stages of use. Thus, present invention device 1 includes a main housing 3 that is a hollow elongated component with a central shaft 7. Main housing 3 has needle 30 in its distal end 9 and plunger 31 partially within its proximal end 11, as shown. Distal end 9 is sealed from the main shaft area except for the opening through which needle 30 passes, as shown. Note that the needle 30 has a typical piercing end 40. Also at the distal end is an endpiece 13 with a needle orifice 15, and, connected to either the endpiece 13 or the main housing 3, is gate 17. In this case gate 17 is a living hinge-type flap valve that is slightly angled so that needle 30, when moved to the right, will push it open, and then when subsequently retracted will allow it to automatically close to its closed rest position due to the living hinge action.

Plunger 31 has a push plate 33, a removal stop 53, an auto lock bar 35 and an elongated ringed overseal 55 made of typical syringe seal material. Stop 53 slides in track 51, preferably sealed with silicone or other gel or gelcoat. Lock bar 35 is optional and is a spring bar. It is pressed in to fit into track 37 past lock receiver 39 for plunger 31 operation. The dimensions are not accurate in the drawings, but the lengths, diameters and volumes of actual construction would be sized so that the seals, stops and in flows and outflows would be in concert.

Main housing 3 also has a drug-receiving fill port 21 with conduit that empties into reservoir 5. There is a cap 57 and a one way flap valve 19. This valve is a one way valve and any equivalent valving may be used in its place, e.g., a one way ball valve. The one way valve allows med 50 (FIG. 2) to flow into the reservoir 5 when plunger 33 is pulled to the left, but not to flow back into the vial by gravity or pressure. See FIG. 2.

Through valve 41 has inlet channel 43 that enters the sliding through the valve wall that is contiguous to and helps establish reservoir 5, and it flows to the inside wall of the shaft of main housing 3. Through valve 41 also has an outlet channel 61 that is apart from (not directly connected to) inlet channel 43, that begins at the sidewall of the valve 41 at the inside wall of the shaft of the main housing 3 and flows to the end wall of valve 41 that faces away from the reservoir 5. Seal 56 is positioned between these two channels to prevent slight accidental med movement when not desired (when the device is not being operated and the valve is in its closed position). Needle 40 is fixed to sliding through valve 41 at through valve outlet channel 61. Spring 45 pushes valve 41 to the left and maintains it in this closed position when the device is not in operation. Stop 23 or other equivalent mechanism, e.g. a stop on the right side of the valve, prevents the valve 41 from traveling any further to the left.

Main housing 3 has a strategically positioned drug release conduit 59 inside the shaft 7, as shown. When plunger 31 is pushed inwardly, see FIG. 4, the mass of med 50 cannot flow out of the reservoir 5 and it acts as a piston to push valve 41 against spring 45 to compress it, and valve 41 moves with needle 30 to the right until both channels 43 and 61 align with drug release conduit 59 (FIG. 4).

When plunger 31 is pushed in further, since valve 41 is in the open position, liquid med will flow through channel 43, through conduit 59, through channel 61 and through needle 30, for med delivery to the end recipient or receiver. See FIG. 5. The plunger 31 may be at least partially transparent and have calibrations for smaller than full barrel dosage delivery.

When the plunger push pressure is released, spring 45 pushes the valve 41 back to its start (rest, closed) position, carrying the needle 30 likewise back to its rest position, and gate 17 automatically closes. Further, lock bar 35 locks into slot 39 of track 37 and the plunger 31 cannot be moved in or out thereafter without first depressing the lock bar 35. The device 1 is fully sealed after use and may be disposed of in accordance with required procedures.

FIG. 7 shows the FIG. 2 present invention device 1, uncut, in the top view position to merely illustrate one possible external design.

FIGS. 8 and 9 show side cut views of another preferred embodiment of a present invention drug delivery device 200 with a sliding through valve, such as is shown above, but has a stationary needle instead of the sliding through valve connected needle described above various stages of use. Present invention device 200 includes a main housing 203 that is a hollow elongated component with a central shaft 207. Main housing 203 has stationary needle 230 in its distal end 209 and plunger 231 partially within its proximal end 211. Needle 230 has a typical piercing end 240. Also at the distal end is an endpiece 213, in this case a needle protective cover that is removed to utilize the device 200 for drug delivery. Endpiece 213 replaces the gate shown in present invention device 1 above.

Plunger 231 has a push plate 233, a removal stop 253, an auto lock bar 235 and an elongated ringed overseal 255 made of typical syringe seal material. It functions similarly to that described above. Stop 253 slides in track 251, preferably sealed with silicone or other gel or gelcoat.

Main housing 203 also has a drug-receiving fill port 221 with conduit that empties into reservoir 225. There is a cap 257 and a one way flap valve 219. This valve is a one way valve and any equivalent valving may be used in its place, e.g., a one way ball valve. The one way valve allows med 250 (FIG. 9) to flow into the reservoir 225 when plunger 233 is pulled to the left, but not to flow back into the vial by gravity or pressure. See FIG. 9. (See also FIG. 2 as a general reference to this step in use. Although device 1 and device 200 are different, their functionality for this step of feeding or withdrawing the med into the main housing is the same.)

Through valve 241 has inlet channel 243 that enters the sliding through the valve wall that is contiguous to and helps establish reservoir 225, and it flows to the inside wall of the shaft of main housing 203. Through valve 241 also has an outlet channel 261 that is apart from (not directly connected to) inlet channel 243, that begins at the sidewall of the valve 241 at the inside wall of the shaft of the main housing 203 and flows to the end wall of valve 241 that faces away from the reservoir 225. Seal 256 is positioned between these two channels to prevent slight accidental med movement when not desired (when the device is not being operated and the valve is in its closed position). Needle 240 is fixed to the main housing with a feed pipe receiver port, while sliding through valve 241 has a feed pipe 265 connected at through valve outlet channel 261. Spring 245 pushes valve 241 to the left and maintains it in this closed position when the device is not in operation. Stop 223 or other equivalent mechanism, e.g. a stop on the right side of the valve, prevents the valve 241 from traveling any further to the left.

Main housing 203 has drug release conduit 259 inside the shaft 207, as shown. When plunger 231 is pushed inwardly, see FIG. 9, the mass of med 250 cannot flow out of the reservoir 225. It acts as a piston to push valve 241 against spring 245 to compress it, and valve 241 moves with feed pipe 265 to its receiver port at fixed needle 230 to the right while both channels 243 and 261 align with drug release conduit 259 (FIG. 9). The device 200 now functions and is operated in the same manner as device 1 above to discharge the med and to have automatic lock up upon release of the plunger 233. The advantages of device 1 described above are likewise achieved with this device 200, and, additionally, the advantages of a fixed needle type device are also inherent herein.

FIG. 10a through FIG. 10d illustrate various stages in the functionality and the methodology of utilization of the present invention drug delivery devices for intravenous system connection, in block diagram format, i.e., present invention devices that utilize IV line connections in place of needles to feed the medication to the patient via the IV system. The external housing of the device is excluded for simplicity, but may be any functional housing, from a syringe type device to a table model instrument, without exceeding the scope of the invention. In FIG. 10a, plunger 300 is positioned in a housing (not shown) adjacent empty reservoir 310, also encompassed by said housing. Connected to the empty reservoir 310 through the housing is fill port 360 with an optional but preferred one way valve. On the opposite side of reservoir 310 from plunger 300 is sliding through-valve 320. Spring 330 pushes valve 320 to the left to maintain valve 320 closed when no pressure is exerted upon it. Gate 350 is generally closed, unless opened by med fluid pushed against it (e.g., a one way ball valve or flap valve) being pushed against it directly or indirectly, or if there is an external gate, unless opened manually. The slide through valve operates in a fashion similar to the FIG. 8 present invention device 200, in that there will be a feed pipe or equivalent connector attached to the sliding through valve and a fixed receiver and outlet.

Identical numbers from FIG. 10a are used for identical block diagram components in FIGS. 1b, 1c and 1d. FIG. 1b illustrates a full reservoir by pulling plunger 300 to the left. FIG. 10c illustrates the force of full reservoir 310 pushing on the sliding through valve 320 when plunger 300 is pushed inwardly, and FIG. 10d shows the medication being delivered as plunger 300 is pushed further inwardly. When plunger 300 is released, the spring 320 decompresses, moves valve 320 to a locked position and gate valve 350 is closed.

Thus, when plunger 300 is pulled to the left, FIG. 1b, the liquid medication from a vial will pass through fill port 360 to reservoir 310 and fill reservoir 310. A one way valve (not shown) prevents liquid med from flowing back into the vial. When plunger 300 is next pushed to the right toward valve 320, FIG. 1c, the med in full reservoir 310 acts as a moving piston to push against sliding through valve 320 and pushes valve 320 against spring 330 to compress the spring 320 until it stops at an open valve position and connects with outlet 340. Next, when plunger 300 is pushed further to the right (pushed in further), FIG. 1d, the med in reservoir 310 is moved out of the reservoir 310, through open valve 320 and out the outlet 340, to deliver the med directly to the IV system of the patient or otherwise. As soon as the nurse or other user releases the push pressure on plunger 300, the spring 330 automatically pushes the valve 320 back to its closed position and gate 350 automatically closes. All aspects of the device are sealed to the outside, preventing drips and evaporative losses.

FIGS. 11 and 12 show side cut views of another preferred embodiment of a present invention drug delivery device 400 with a sliding through valve, such as is shown above, but has a stationary IV or other port connector at its distal end instead of a needle. Present invention device 400 includes a main housing 403 that is a hollow elongated component with a central shaft 407. Main housing 403 has stationary outlet 440 in its distal end 409 and plunger 431 partially within its proximal end 411. Outlet 440 has a typical threaded connection end, as shown. This could be an inside or and outside threading, depending upon the connector to which it may be attached. Plunger 431 has a push plate 433, a removal stop 453, an auto lock bar 435 and an elongated ringed overseal 455 made of typical syringe seal material. It functions similarly to those previously described in the Figures above. Stop 453 slides in track 451, preferably sealed with silicone or other gel or gelcoat.

Main housing 403 also has a drug-receiving fill port 421 with conduit that empties into reservoir 5. There is a cap 457 and a one way flap valve 419. This valve is a one way valve and any equivalent valving may be used in its place, e.g., a one way ball valve. The one way valve allows med 50 (FIG. 12) to flow into the reservoir 425 when plunger 33 is pulled to the left, but not to flow back into the vial by gravity or pressure. See FIG. 12. (See FIG. 2 as a general reference to this step in use. Although device 1 and device 400 are different, their functionality for this step of feeding from the med source or withdrawing the med into the main housing from the med source, is the same.)

Through valve 441 has inlet channel 443 that enters the sliding through the valve wall that is contiguous to and helps establish reservoir 425, and it flows to the inside wall of the shaft of main housing 403. Through valve 441 also has an outlet channel 461 that is apart from (not directly connected to) inlet channel 443, that begins at the sidewall of the valve 241 at the inside wall of the shaft of the main housing 203 and flows to the end wall of valve 241 that faces away from the reservoir 425. Seal 456 is positioned between these two channels to prevent slight accidental med movement when not desired (when the device is not being operated and the valve is in its closed position). Outlet 440 is fixed to the main housing with a feed pipe receiver port, while sliding through valve 441 has a feed pipe 465 connected at through valve outlet channel 461. Spring 445 pushes valve 441 to the left and maintains it in this closed position when the device is not in operation. Stop 423 or other equivalent mechanism, e.g. a stop on the right side of the valve, prevents the valve 441 from traveling any further to the left.

Main housing 403 has drug release conduit 459 inside the shaft 407, as shown. When plunger 431 is pushed inwardly, see FIG. 12, the mass of med 450 cannot flow out of the reservoir 425. It acts as a piston to push valve 441 against spring 445 to compress it, and valve 441 moves with feed pipe 465 to its receiver port at wall 447 to the right while both channels 443 and 461 align with drug release conduit 430 and ball valve 413 (FIG. 12). The device 400 now functions and is operated in the same manner as device 200, except that med fluid pressure against ball valve 413 opens it to deliver medication through outlet 440 to the patient IV port or other connection. After discharge the med, the nurse or doctor releases plunger pressure to effect automatic lock up of the valve 441 and the ball 413. The advantages of device 1 described above are likewise achieved with this device 200, and, additionally, the advantages of a fixed feed device are also inherent herein.

Figure 13:
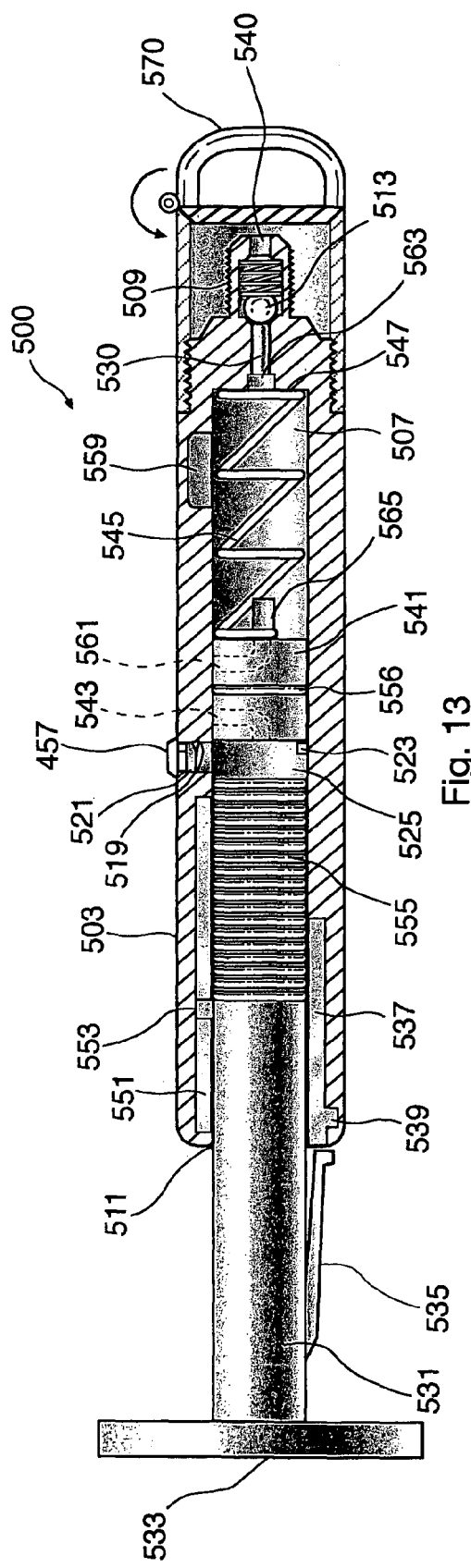
Figure 14:
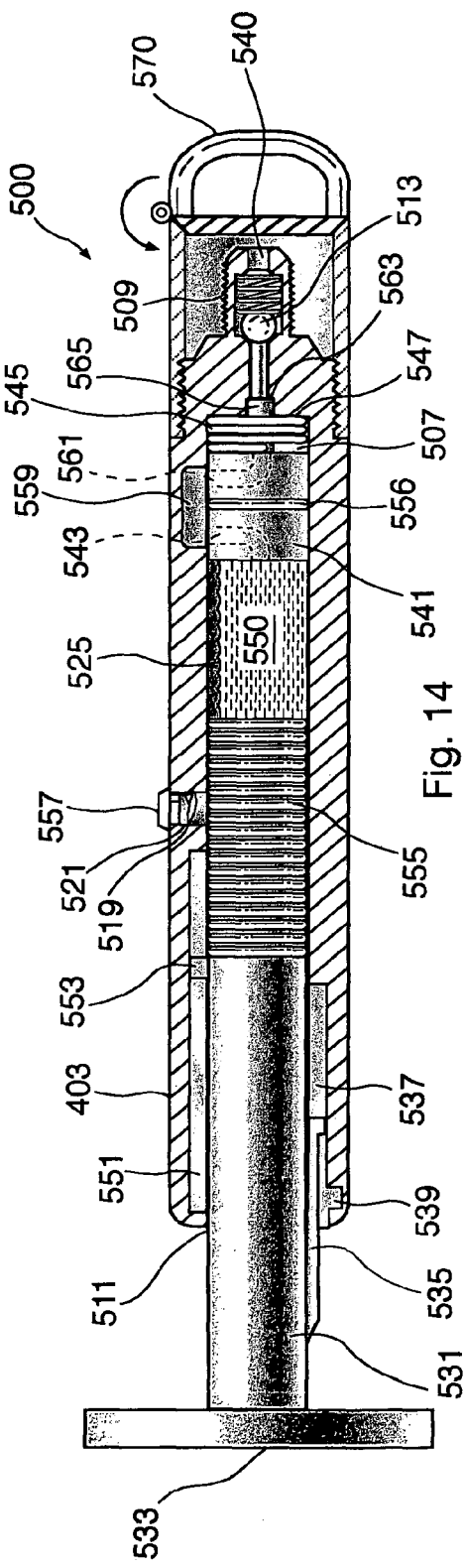

FIGS. 13 and 14 show side cut views of another preferred embodiment of a present invention drug delivery device 500 with a sliding through valve, such as is shown in FIGS. 11 and 12 above, but has a flap valve on a stationary IV or other port connector at its distal end instead of an exposed connector. Present invention device 500 includes all of the elements, components and functionality of the device 400 described in the preceding four paragraphs and has flap valve 570, as well. All of the device 400 parts in FIGS. 11 and 12 are repeated herein in FIGS. 13 and 14, except that these are number in the 500 series instead of the 400 series. Thus, the part numbered 503 in FIGS. 13 and 14 is the same as the part numbered 403 in FIGS. 11 and 12, etc. Flap valve 507 has a handle that a user would simply lift up to screw or attach the connector 540 to the IV or other connection port. Because this flap valve 570 has a spring or, as in this drawing is a living spring with the closed position being its rest position, when the device 500 is disconnected from the IV or other connection, flap valve 570 snaps closed and dripping and evaporative losses are prevented.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims. Fore example, the present invention devices may take the form of a stationary device or table model rather than a hand held device as shown. All of the internal components and functions would be the same except that the external housing would have a stationary bottom. Such an alternative mechanism could be hand operated or could be computer controlled and operated. A computer could operate a drive connected to the plunger and it could perform all of the plunger steps above. It could also be calibrated to complete the plunger movement in the step shown in FIGS. 1*d* and 10*d* above a specified length to correspond to a specified dosage.

What is claimed is:

1. A drug delivery device, which comprises:
   - (a.) a main housing having a linear shaft with a proximal end, a distal end and a side wall, and having a drug holding reservoir within said shaft toward said proximate end, and having a drug release conduit located on said shaft side wall toward said distal end, and having a shaft outlet located at said distal end of said shaft;
   - (b.) a fill port, the fill port being connected to a fill port inlet conduit;
   - (c.) said fill port inlet conduit connected to said shaft at said holding reservoir;
   - (d.) a one-way valve located within said inlet conduit between said fill port and said holding reservoir positioned to permit flow from to said holding reservoir and not the opposite;
   - (e.) a slide valve having a proximal end, said proximal end being a first wall, and having a distal end, said distal end being a second wall, said side valve having a side wall connecting said distal end and said proximal end, said slide valve first wall facing toward said holding reservoir and said slide valve second wall facing away from said holding reservoir, said first wall having a liquid inlet channel connected to said side wall, and said second wall having a liquid outlet channel connected to said side wall, said liquid inlet channel and said liquid outlet channel being in proximity to one another and not directly connected to one another, and having a seal located on said side wall between said liquid inlet channel and said liquid outlet channel, said slide valve being located in said shaft and adapted for movement within said shaft from a first position to a second position and vice versa;
     - wherein when said slide valve is in said first position, said slide valve is away from said drug release conduit and said drug holding reservoir is closed from said drug release conduit, and when said slide valve is in said second position, said slide valve is located at said drug release conduit and said drug release conduit is open to permit liquid drug to pass from said drug holding reservoir through said slide valve via, in sequence, said liquid inlet channel, said drug release conduit and said liquid outlet channel, to a needle;
   - (f.) a needle functionally connected to said slide valve liquid outlet channel;
   - (g.) a plunger being partially and slideably located in said proximal end of said shaft, said plunger having a rod and a piston, said plunger having sufficient length to be moved from a first plunger position to a second plunger position to a third plunger position, and vice versa;
   - (h.) a spring located in said shaft at said distal end of said slide valve biasing said slide valve to its first position;
     - wherein, when the drug fill port is connected to a liquid drug source, and the plunger is pulled back from the first position to the second position, the liquid drug will be moved from its source into the fill port through said fill port inlet conduit into the drug holding reservoir, and when said plunger is pushed forward from its second position toward its first position, said spring will compress and said slide valve will move from its closed, first position to its open, second position in alignment with said drug release conduit and said needle will move to a functional position through said shaft outlet, and when said plunger is moved from its second position to its third position, said spring remains compressed and the force of the plunger will advance the liquid drug through said liquid inlet channel, through said drug outlet conduit, through said liquid outlet channel and through said needle for injection thereof.

2. The drug delivery device of claim 1 wherein said needle is directly connected to said slide valve and travels with said slide valve from a first position to a second position and vice versa.

3. The drug delivery device of claim 2 wherein when said slide valve is in its first position, said needle is fully contained within said shaft, and when said slide valve is in its second position, said needle is partially extended through said shaft outlet and beyond said distal end of said shaft so as to be positioned for injection.

4. The drug delivery device of claim 1 wherein said distal end of said shaft includes a gate that is closed when in its rest position when said needle is fully contained within said shaft and opens when said valve and needle are moved from said first position to said second position and said needle is partially extended.

5. The drug delivery device of claim 1 wherein said device further includes a child resistant mechanism on at least one of said shaft and said plunger, that has a lock position to prohibit movement of said slide valve from said first position to said second position and a go position wherein said child resistant mechanism must be engaged into said go position from said lock position to permit movement of said plunger to move said slide valve form said first position to said second position.

6. The drug delivery device of claim 1 wherein said needle is physically separate from said slide valve and is stationary relative to said shaft until said slide valve is in its second position.

7. The drug delivery device of claim 1 wherein said device includes a catch mechanism to prevent removal of said plunger from said shaft once it is positioned therein.

8. The drug delivery device of claim 1 wherein said main housing includes a keyway for said slide valve to position said slide valve inlet channel and outlet channel in bias with said drug release conduit of said main housing.

9. The drug delivery device of claim 1 wherein said main housing is comprised of at least two assembled sections.

10. A methodology for drug delivery utilizing a manual drug delivery device, which comprises the steps of:
   - A.) loading a drug holding reservoir of a manual drug delivery device with a predetermined amount of a liquid drug and sealing said liquid drug in said drug holding reservoir, said manual drug delivery device including the following structure:
- (a.) a main housing having a linear shaft with a proximal end, a distal end and a side wall, and having a drug holding reservoir within said shaft toward said proximal end, and having a drug release conduit located on said shaft side wall toward said distal end, and having a shaft outlet located at said distal end of said shaft;
- (b.) a fill port, the fill port being connected to a fill port inlet conduit;
- (c.) said fill port inlet conduit connected to said shaft at said holding reservoir;
- (d.) a one-way valve located within said inlet conduit between said inlet port and said holding reservoir positioned to permit flow to said holding reservoir and not the opposite;
- (e.) a slide valve having a proximal end, said proximal end being a first wall, and having a distal end, said distal end being a second wall, said side valve having a side wall connecting said distal end and said proximal end, said slide valve first wall facing toward said holding reservoir and said slide valve second wall facing away from said holding reservoir, said first wall having a liquid inlet channel connected to said side wall and said second wall having a liquid outlet channel connected to said side wall, said first wall and said second wall being in proximity to one another and not directly connected to one another, and having a seal located on said side wall between said liquid inlet channel and said liquid outlet channel, said slide valve being located in said shaft and adapted for movement within said shaft from a first position to a second position and vice versa;
- wherein when said slide valve is in said first position, said slide valve is away from said drug release conduit and said drug holding reservoir is closed from said drug release conduit, and when said slide valve is in said second position, said slide valve is located at said drug release conduit and said drug release conduit is open to permit liquid drug to pass from said drug holding reservoir through said slide valve via, in sequence, said liquid inlet channel, said drug release conduit and said liquid outlet channel, to a needle;
- (f.) a needle functionally connected to said slide valve liquid outlet channel;
- (g.) a plunger being partially and slideably located in said proximal end of said shaft, said plunger having a rod and a piston, said plunger having sufficient length to be moved from a first plunger position to a second plunger position and to a third position, and vice versa;
- (h.) a spring located in said shaft at said distal end of said slide valve biasing said slide valve to its first position;
- B.) positioning said device adjacent a drug injection receiver;
- C.) moving said plunger forward from its second position toward its first position, thereby compressing said spring and moving said slide valve from its closed, first position to its open, second position in alignment with said drug release conduit and further thereby moving said needle to a functional position through said shaft outlet; and,
- D.) next moving said plunger from its second position to its third position, said spring remains compressed and the force of the plunger thereby advancing the liquid drug through said liquid inlet channel, through said drug outlet conduit, through said liquid outlet channel and through said needle for injection thereof into said injection receiver.

11. The drug delivery methodology of claim 10 wherein said slide valve includes a valve conduit that connects from said drug outlet conduit to said needle when said slide valve is in its second position so as to permit said drug to flow therethrough.

12. The drug delivery methodology of claim 10 wherein said needle is directly connected to said side valve and travels with said slide valve from its first position to its second position and vice versa when said step C. is effectuated.

13. The drug delivery methodology of claim 12 wherein when said slide valve is in its first position, said needle is fully contained within said shaft, and when said step C. is effectuated, said slide valve is moved to its second position and said needle is partially extended beyond said distal end of said shaft so as to be positioned for injection.

14. The drug delivery methodology of claim 13 wherein said distal end of said shaft includes a gate that is closed when in its rest position when said needle is fully contained within said shaft and opens when step C. is effectuated, said valve and needle are moved from said first position to said second position and said needle is partially extended.

15. The drug delivery methodology of claim 10 wherein said device further includes a child resistant mechanism that has a lock position to prohibit movement of said slide valve from said first position to said second position and a go position and said methodology includes the step of engaging said child resistant mechanism by moving it into said go position from said lock position to permit movement of said slide valve form said first position to said second position.

16. The drug delivery methodology of claim 10 wherein said needle is physically separate from said slide valve and is stationary relative to said shaft.

17. The drug delivery methodology of claim 10 wherein said device includes a catch mechanism to prevent removal of said plunger from said shaft once it is positioned therein.

18. The drug delivery methodology of claim 10 which further includes the subsequent step of releasing said plunger so that the first spring and second spring are uncompressed and said slide valve returns to its first position.

* * * * *